United States Patent
Johnson et al.

(10) Patent No.: US 9,155,740 B2
(45) Date of Patent: Oct. 13, 2015

(54) COMPOSITIONS AND METHODS FOR TREATMENT AND PREVENTION OF HYPERURICEMIA RELATED HEALTH CONSEQUENCES

(76) Inventors: Richard J. Johnson, Gainesville, FL (US); Takahiko Nakagawa, Gainesville, FL (US)

( * ) Notice: Subject to any disclaimer, the term of this patent is extended or adjusted under 35 U.S.C. 154(b) by 0 days.

(21) Appl. No.: 13/364,313

(22) Filed: Feb. 1, 2012

(65) Prior Publication Data

US 2012/0220607 A1  Aug. 30, 2012

Related U.S. Application Data

(63) Continuation of application No. 11/995,943, filed on Jan. 17, 2008, which is a continuation-in-part of application No. PCT/US2005/025910, filed on Jul. 21, 2005, and a continuation-in-part of application No. PCT/US2006/020998, filed on May 31, 2006.

(60) Provisional application No. 60/589,921, filed on Jul. 21, 2004.

(51) Int. Cl.
*A01N 43/90* (2006.01)
*A61K 31/519* (2006.01)
*A61K 31/426* (2006.01)
*A61K 31/4439* (2006.01)

(52) U.S. Cl.
CPC .............. *A61K 31/519* (2013.01); *A61K 31/426* (2013.01); *A61K 31/4439* (2013.01)

(58) Field of Classification Search
CPC ............. A61K 31/426; A61K 31/4439; A61K 31/519; A61K 31/522
See application file for complete search history.

(56) References Cited

U.S. PATENT DOCUMENTS

| 6,353,009 B1 | 3/2002 | Fujiwara et al. |
| 2002/0019360 A1* | 2/2002 | Kivlighn et al. ............... 514/44 |
| 2010/0120796 A1 | 5/2010 | Johnson et al. |

FOREIGN PATENT DOCUMENTS

| CN | 1615875 | 5/2005 |
| EP | 11365073 | 9/2001 |
| WO | WO 02/00210 | 1/2002 |
| WO | WO 2005/063788 | 7/2005 |
| WO | WO 2006/012438 | 2/2006 |

OTHER PUBLICATIONS

Cavallo-Perin et al, European Journal of Clinical Investigation (2001) 31, 318-321.*
Butler, Hypertension, vol. 35, pp. 746-751, 2000.*
Hayden et al, Nutrition & Metabolism 2004, 1:10 p. 1-15.*
Lai et al. "Epidemiology of Fatty Liver in a Hospital based Study in Taiwan", Southern Medical Journal, vol. 95, No. 11, pp. 1288-1292.

* cited by examiner

*Primary Examiner* — Wu-Cheng Winston Shen
*Assistant Examiner* — Jean Cornet
(74) *Attorney, Agent, or Firm* — Timothy H. Van Dyke; Beusse, Wolter, Sanks & Maire, PLLC

(57) ABSTRACT

Disclosed herein are methods of delaying the onset or treating diabetes that comprises administering a uric acid lowering agent. The inventors have made the remarkable discovery that elevated uric acid levels are not a corollary to insulin resistance, but rather a primary mediator of insulin resistance. Specifically exemplified are methods that involve administering to a patient susceptible to development of diabetes a composition comprising a uric acid lowering agent in a regimen that maintains serum uric acid levels below at least 5.5 mg/dl, or below at least 5.2 mg/dl.

3 Claims, 11 Drawing Sheets

COMPOSITIONS AND METHODS FOR TREATMENT AND PREVENTION OF HYPERURICEMIA RELATED HEALTH CONSEQUENCES

CROSS-REFERENCE TO RELATED APPLICATIONS

This application is a continuation of U.S. application Ser. No. 11/995,943 filed Jan. 17, 2008, which is a continuation in part of International Application No. PCT/US05/25910; filed Jul. 21, 2005 and a continuation in part of International Application No. PCT/US06/20998; filed May 31, 2006. This application also claims benefit of the Jul. 21, 2004, filing date of U.S. provisional patent application No. 60/589,921.

The research which forms the basis of this patent disclosure was supported in part by National Institutes of Health Grant No. HL-68607 (NIH RO-1). Accordingly, the U.S. Government has certain rights in this invention.

BACKGROUND OF THE INVENTION

Diabetes mellitus is characterized by a broad array of physiologic and anatomic abnormalities, for example, altered glucose disposition, hypertension, retinopathy, abnormal platelet activity, aberrations involving large, medium and small sized vessels, and other problems encountered in diabetic patients. Diabetes is classified into two categories: primary and secondary. Primary diabetes includes: 1) Insulin-dependent diabetes mellitus (IDDM, Type 1), 2) Non-insulin-dependent diabetes mellitus (NIDDM, Type 2) including a) Nonobese NIDDM, b) Obese NIDDM and c) Maturity-onset diabetes of the young. Primary diabetes implies that no associated disease is present, while in the secondary diabetes some other identifiable condition causes or allows a diabetic syndrome to develop, for example, 1) Pancreatic disease, 2) Hormonal abnormalities, 3) Drug or chemical induced, 4) Insulin receptor abnormalities, 5) Genetic syndromes and 6) Others.

Insulin dependence in this classification is not equivalent to insulin therapy, but means that the patient is at risk for ketoacidosis in the absence of insulin. It has been suggested that the terms insulin-dependent and non-insulin-dependent describe physiologic states (ketoacidosis-prone and ketoacidosis-resistant, respectively), while the terms Type 1 and Type 2 refer to pathogenetic mechanisms (immune-mediated and non-immune-mediated, respectively). Using this classification, three major forms of primary diabetes are recognized: (1) type 1 insulin-dependent diabetes, (2) type 1 non-insulin-dependent diabetes, and (3) type 2 non-insulin-dependent diabetes.

Secondary forms of diabetes encompass a host of conditions such as pancreatic disease, hormonal abnormalities, genetic syndromes, and others.

Insulin-dependent diabetes mellitus often develops in childhood or adolescence while the onset of NIDDM generally occurs in middle or late life. Patients with NIDDM are usually overweight and constitute 90 to 95 percent of all diabetics. IDDM results from the destruction of beta cells by an autoimmune process that may be precipitated by a viral infection. NIDDM is characterized by a gradual decline in beta cell function and varying degrees of peripheral resistance to insulin. The annual incidence of IDDM ranges from 10 cases per 100,000 persons for nonwhite males to 16 cases per 100,000 persons for white males. LaPorte, R. E. et al., 1981, Diabetes 30: 279. The prevalence of NIDDM increases with age, especially after age 45 and is higher among blacks than whites and certain populations such as Asian Indians living in South Africa and England. Malter, H. M. et al., 1985, Br. Med. J. 291: 1081. Gestational diabetes occurs in 2.4 percent of all pregnancies in the United States annually. Freinkel, N. et al., 1985, N. Engl. J. Med. 313: 96. Pregnancy is also a state of insulin resistance. This insulin resistance is exacerbated in gestational diabetes which may predispose patients to the various hypertensive syndromes of pregnancy associated with Type 2 NIDDM. Bardicef, M. et al., 1995, Am. J. Gynecol. 172: 1009-1013.

Current therapies for IDDM include insulin therapy, and for NIDDM will include dietary modification in a patient who is overweight and hypoglycemic agents, e.g., tolbutamide, chlorpropamide, acetohexamide, tolazamide, glipizide and glyburide, all of which act by stimulating the release of insulin from the beta cells. Also, thiazolidone drugs like rosiglitazone are being used to treat insulin resistance.

Insulin resistance and hyperuricemia are considered a part of the 'metabolic syndrome' or 'syndrome X' of obesity, insulin resistance, hypertriglyceridemia and hyperuricemia, which underlies the pathogenesis of type II diabetes. Insulin resistance is an impaired metabolic response to our body's own insulin so that active muscle cells cannot take up glucose as easily as they should. The condition can exist unrecognized and metabolic damage can occur before a full blown Type 2 diabetes is finally diagnosed. Insulin resistant diabetics are 2-5 times more likely to die from heart attack or stroke than are non diabetics. Currently metabolic syndrome is epidemic both in the United States and throughout the world, resulting in exponential increases in health care cost and causing great morbidity and mortality due to the increased risk for cardiovascular and renal disease in this population. Most studies suggest that the epidemic is due to the adaptation of 'Westernized diet'—this diet is also known to increase our risk for gout (Johnson R J, Rideout B: Uric acid and diet: insights into the Epidemic of Cardiovascular Disease. N Engl J Med (editorial) 2004; 350:1071-1074).

It has widely been assumed that the rise in serum uric acid associated with insulin resistance is due to the effect of insulin to increase urate reabsorption in the renal tubule, and hence it had been assumed that the hyperuricemia associated with insulin resistance does not have a causal role in the syndrome.

SUMMARY OF THE INVENTION

The inventors have made the remarkable discovery that elevated levels of uric acid is a primary mediator of insulin resistance. The subject invention provides a new approach to combating the epidemic of the metabolic syndrome. In one embodiment, the subject invention provides an approach to preventing and/or treating one or more metabolic syndrome related characteristics.

In a specific embodiment, the subject invention pertains to methods of administering a uric acid lowering agent (UALA) to a patient susceptible to developing insulin resistance or suffering from insulin resistance. As part of the medical treatment, serum samples may be obtained and tested so that serum uric acid levels may be monitored in conjunction with the administration of the UALA.

In another embodiment, the subject invention provides an approach to preventing and/or treating metabolic syndrome related obesity. In a specific embodiment, the subject invention pertains to methods of administering a uric acid lowering agent (UALA) to a patient susceptible to developing or suffering from metabolic syndrome related obesity.

In another embodiment, the subject invention provides an approach to reducing the risk of developing, delaying the onset of and/or treating nonalcoholic fatty liver disease.

In another embodiment, the subject invention provides an approach to reducing the risk of developing, delaying the onset of and/or diabetic nephropathy.

DETAILED DESCRIPTION OF THE INVENTION

Figure 1:
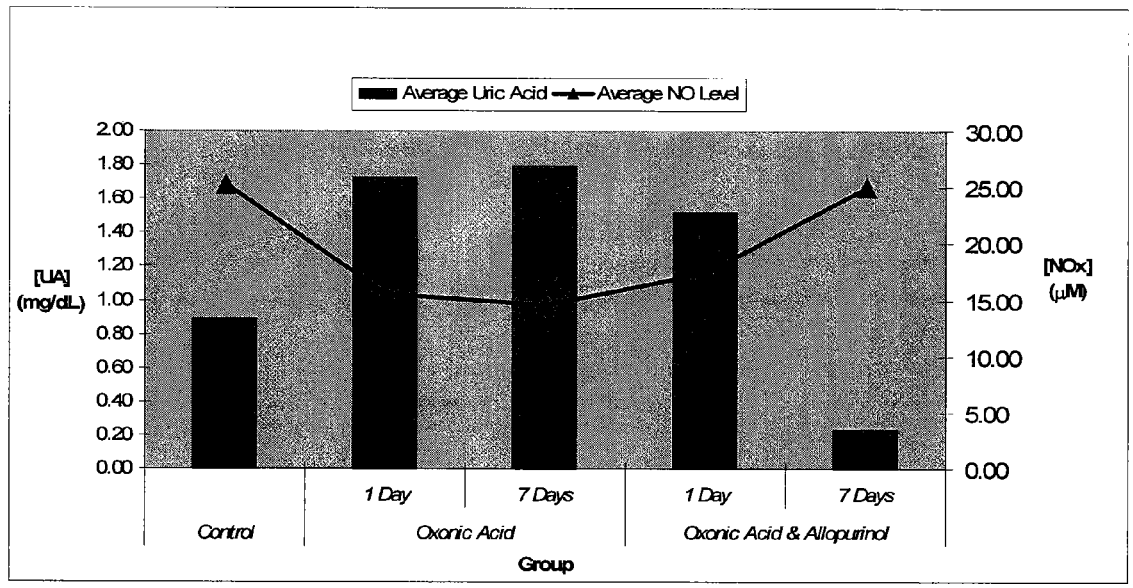
FIG. 1 is a graph showing the relationship of serum uric acid and serum nitrites at 1 and 7 Days of hyperuricemic induced rats. Serum was analyzed for uric acid concentration and nitrites/nitrates ($NO_x$) by chemiluminescence method.

The pharmaceutical compositions provided herein contain therapeutically effective amounts of one or more agents to lower uric acid that are useful in the treatment or prevention of insulin resistance. The inventors have discovered that hyperuricemia plays a critical role in causing insulin resistance.

The term "uric acid lowering agent" or UALA refers to substances known to lower serum uric acid levels in mammals. Typically, the UALA may limit serum uric acid levels by at least about 0.2 mg/dl. UALAs include, but are not limited to, xanthine oxidase inhibitors such as allopurinol, hydroxyakalone, TEI-6720, carprofen, febuxostat, and y-700; uricosurics such as benziodarone, benzbromarone, probenecid; uricase derivatives such as Rasburicase and Pegylated uricase; gene based therapies such as uricase overexpression or blockade of URAT-1; a supplement of the uricase protein which might be delivered as a conjugate with polyethylene glycol or another delivery system; and a urate transport channel inhibitor.

The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that reduces serum uric acid levels at least 0.5 mg/dl to be equal to or less than 5.5 mg/dl. In a most preferred embodiment, effective amount is such as to lower serum uric acid levels to less than or equal to 5.5 mg/dl and more than or equal to 3.5 mg/dl. Preferably still, the effective amount is such as to lower serum uric acid levels to less than or equal to 5.2 mg/dl and more than or equal to 4.0 mg/dl. It is known that uric acid acts as antioxidant in the body. Epidemiological studies performed by the inventor have uncovered that the positive effects of avoiding insulin resistance are achieved by lowering serum uric acid levels to at least 5.5 mg/dl. However, the positive effects are largely negated as serum uric acid levels fall below 4.0 mg/dl. At levels below 4.0 mg/dl, the loss of antioxidant activity of uric acid may actually predispose to an increased incidence of cardiovascular disease and mortality. The UALA may be administered concomitantly or sequentially with one or more known antioxidants, such as, but not limited to, vitamin C, alpha-lipoic acid, Vitamin E, beta carotene, selenium, zinc, carnosine, green tea, soy and isoflavones, tempol, etc. Such combination may be beneficial regardless of uric acid levels, but may be particularly helpful if dosages of UALA are administered that lower the uric acid below 4.5 mg/dl.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

The term "average serum uric acid level(s)" as used herein refers to an average of two or more uric acid readings obtained from a patient. The two or more uric acid readings may be taken within hours of each other. Preferably, the two or more readings are obtained at least a week from each other.

The term "regimen" as used herein refers to an administration of two or more dosages sequentially spaced in time so as to maintain average serum uric acid levels at a predetermined level. The space in time is preferably 3 or more hours. The regimen may be based on empirically determined optimal dosages. Naturally, it goes without saying that the administration of UALA according to a regimen 'so as to maintain (or effective to maintain) average serum uric acid levels' at a predetermined level is understood to mean that readings from a patient are not necessarily obtained, but rather that the regimen is designed to be effective to maintain serum uric acid levels at a desired average level over a period of time whether or not such average is actually determined for a given patient.

Asymptomatic hyperuricemia refers to the state of hyperuricemia without clinical gout, renal stones or tophi. Hyperuricemia is traditionally considered to pertain to serum uric acid levels 7.0 mg/dL and higher, but as is noted herein, for purposes of embodiments of the present invention, hyperuricemia is considered to pertain to serum uric acid levels higher than 5.5 mg/dL. Conventional wisdom dictates that asymptomatic hyperuricemia is benign and should not medically be treated (Harris et al., 1999 Feb. 15; 59(4):925-34). The inventors have elucidated that chronic hyperuricemia can promote the onset of the metabolic syndrome, diabetic nephropathy, and non-alcoholic fatty liver disease and that lowering and maintaining levels of uric acid to 5.5 and below can reduce the onset of such health issues.

In addition, the compounds may be formulated as the sole pharmaceutically active ingredient in the composition or may be combined with other active ingredients. Liposomal suspensions, including tissue-targeted liposomes, particularly tumor-targeted liposomes, may also be suitable as pharmaceutically acceptable carriers. These may be prepared according to methods known to those skilled in the art. For example, liposome formulations may be prepared as described in U.S. Pat. No. 4,522,811.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems (see, e.g., Rosenthal et al. (1996) Antimicrob. Agents Chemother. 40(7):1600-1603; Dominguez et al. (1997) J. Med. Chem. 40:2726-2732; Clark et al. (1994) Molec. Biochem. Parasitol. 17:129; Ring et al. (1993) Proc. Natl. Acad. Sci. USA 90:3583-3587; Engel et al. (1998) J. Exp. Med. 188(4):725-734; Li et al. (1995) J. Med. Chem. 38:5031) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to lower uric acid concentrations at least 0.5 mg/dl to achieve 5.5 mg/dl or lower serum uric acid levels.

Typically a therapeutically effective dosage should produce a serum concentration of active ingredient of from about 0.1 ng/ml to about 50-100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Preferred pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for reducing uric acid at or below 5.5 mg/dl. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, preferably 0.1-85%, typically 75-95%.

The active compounds or pharmaceutically acceptable derivatives may be prepared with carriers that protect the compound against rapid elimination from the body, such as time release formulations or coatings.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound of formula I in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, preferably 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined 4. Topical Administration Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as transdermal patches and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Articles of Manufacture

The compounds or pharmaceutically acceptable derivatives may be packaged as articles of manufacture containing packaging material, a compound or pharmaceutically acceptable derivative thereof provided herein, which is effective for reducing serum uric levels.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,352. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated for treatment and prevention of insulin resistance.

It has recently been reported that raised uric acid levels do not impair endothelial function in humans. Waring et al., *Heart* 2004, 90:155-159. The inventors believe that this report does not fully reveal the effects of raised uric acid levels in the blood. Waring et al reported that the infusion of uric acid into the forearm vein of humans does not impair endothelial function as measured by brachial artery reactivity. However, the authors examined the effect immediately after infusion of uric acid, and it remains possible that the effect on NO production is delayed. Indeed, with experimental hyperuricemia, hypertension does not develop until several weeks after the uric acid is raised. Contrary to the Waring et al. report, the inventors believe that uric acid does indeed impair endothelial dysfunction and as a result NO production is impaired.

EXAMPLE 1

Hyperuricemia Induces Endothelial Dysfunction by Inhibiting the Production of NO in rats.

Methods

Male Sprague-Dawley rats were housed in standard conditions and fed normal diets. Hyperuricemia was induced with an uricase inhibitor, oxonic acid (OA; 750 mg/kg/day), by gavage, with control rats receiving vehicle. Allopurinol (AP) was used to block hyperuricemia by placing AP in the drinking water (150 mg/L). Rats were divided into four groups: (1) Control, (2) AP only, (3) OA only, and (4) OA+AP. Systolic blood pressure was measured using a tail-cuff sphygmomanometer. The amount of drinking water consumed and changes in body weight were noted. Rats were sacrificed at one and seven days. Serum was analyzed for uric acid concentration and nitrites/nitrates ($NO_x$) by chemiluminescence method. (Prabhakar SS: Inhibition of mesangial iNOS by reduced extracellular pH is associated with uncoupling of NADPH oxidation. *Kidney Int* 61:2015-2024, 2002). Statistical analysis between subgroups was performed using ANOVA.

Results

Figure 2:
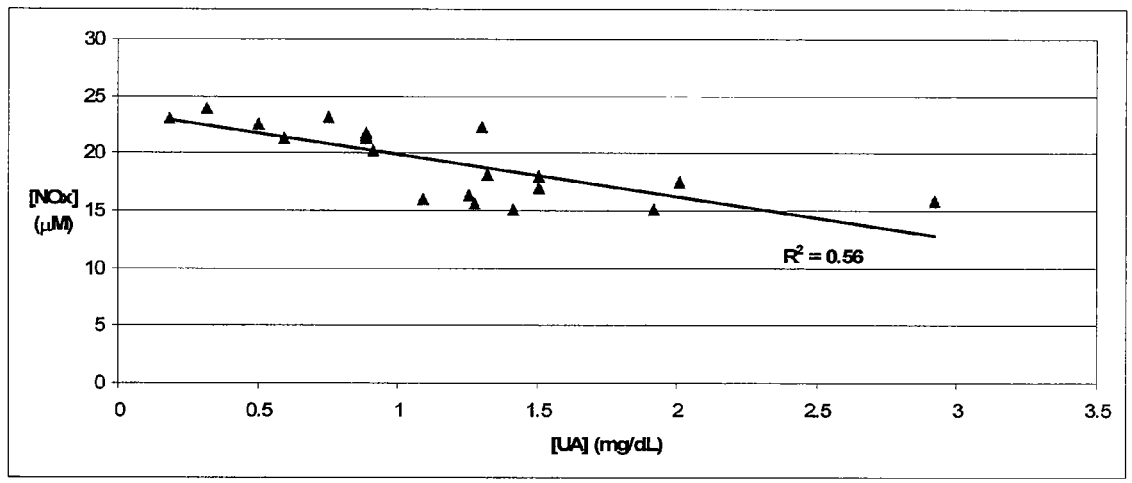
FIG. 2 represents a graph that shows the linear correlation of serum uric acid and serum nitrites.

There was no difference in the amount of water consumed and the change in body weight between the three groups over seven days. OA induced a mild hyperuricemia at both 1 day ($1.7 \pm 0.7$ vs. $0.8 \pm 0.4$ mg/dL in OA vs. Control, $p<0.05$) and 7 days ($1.8 \pm 0.4$ vs. $0.9 \pm 0.7$ mg/dL in OA vs. Control, $p<0.05$). AP only had a mild and non-significant effect on serum uric acid concentrations at day 1 ($1.52 \pm 0.3$ mg/dL, p=NS), but effectively reversed the hyperuricemia at 7 days ($0.3 \pm 0.2$ mg/dL, $p<0.001$). Serum nitrites and nitrates ($NO_x$) were reduced by 40-50% in hyperuricemic rats at both 1 day ($15.6 \pm 0.4$ vs. $22.6 \pm 1.0$ µmol/L in OA vs. Control, $p<0.001$) and 7 days ($14.6 \pm 1.1$ vs. $27.5 \pm 1.3$ µmol/L in OA vs. Control, $p<0.001$). This decrease in $NO_x$ was improved slightly by AP at 1 day ($17.4 \pm 0.8$ µmol/L, $p<0.001$) and reversed completely at 7 days ($25.0 \pm 0.8$ µmol/L, $p<0.001$). (FIG. 1.) There was also a direct linear correlation between serum UA and $NO_x$ (FIG. 2). Rats treated with AP alone did not show a significant change in either serum UA or $NO_x$ concentration. Rats treated with OA also showed a trend toward higher systolic blood pressure at 7 days ($178 \pm 18$ vs. $158 \pm 16$ vs. $147 \pm 11$ mm Hg in OA vs. Control vs. OA/AP, p=NS).

Conclusions

Most mammals have the enzyme uricase that degrades uric acid to allantoin with the generation of oxidants. In humans, uricase is mutated resulting in higher uric acid levels. Rats administered an uricase inhibitor (oxonic acid) develop mild hyperuricemia, hypertension, and vascular disease that is mediated by activation of the renin-angiotensin system, a loss of macula densa NO synthase, and the development of microvascular disease (Mazzali M, Hughes J, Kim Y G, Jefferson J A, Kang D H, Gordon K L, Lan H Y, Kivlighn S, Johnson R J: Elevated uric acid increases blood pressure in the rat by a novel crystal-independent mechanism. *Hypertension* 38:1101-1106, 2001). In this study, it was demonstrated that hyperuricemic rats have a fall in serum nitrites (a reflection of NO production) that is reversed by allopurinol. Furthermore, there was a direct linear correlation between serum uric acid and serum nitric oxide. The induction of hyperuricemia also showed a trend towards increased systolic blood pressure. This data shows that hyperuricemia leads to endothelial dysfunction in the rat. As discussed briefly above, this is a contrary conclusion to that was earlier reported by Waring et al which concluded that the infusion of uric acid into humans does not impair endothelial function (Waring W S, Adwani S H, Breukels O, Webb D J, Maxwell S R: Hyperuricaemia does not impair cardiovascular function in healthy adults. *Heart* 90:155-159, 2004). However, these studies did not measure nitric oxide levels nor mention effects of sustained hyperuricemia on endothelial-dependent vasodilatation.

Without being held to any specific mechanism, the inventors believe that raised serum uric acid levels ultimately lead to insulin resistance mediated by impairment of endothelial function and inhibition of NO production. As support for this mechanistic theory, the inventors cite to Cook et al., *Swiss Med Wkly*, 2003, 133:360-363, which shows that knock-out mice harboring a genetic defect for endothelial nitric oxide synthase develop many of the abnormalities associated with the metabolic syndrome. Accordingly, it is the inventors' position that insulin resistance, and other metabolic related characteristics, results from raised serum uric acid levels, likely caused by the high sugar, fructose-generating western diet, which results in endothelial dysfunction and inhibition of NO production, and ultimately to insulin resistance. Thus, controlling a person's average serum uric acid levels by administration of UALA will have the dramatic affect of delaying the onset of the characteristics of the metabolic syndrome, namely insulin resistance, obesity and hypertriglyceridemia.

According to another embodiment, the subject invention pertains to a method of determining the uric acid increasing load per mass of food. The method may comprise the administration of a quantity of a food item and determination of the affect of such administration on the uric acid levels of such food. Thus, one or more food items are tested and the information is used to generate a uric acid increasing index (or 'UA index'). WO-A 2005040752 and U.S. Patent Pub No. 2004043106 are incorporated by reference, which describes methodology for establishing glycemic loads of foods. The teachings of such publication may be easily adaptable to producing correlating types of information relating to Uric Acid generating loads of foods, including fluids.

EXAMPLE 2

Metabolic Syndrome Characteristics Are Treated by Normalizing Uric Acid Levels

Methods

In Vivo Studies.

Treatment of fructose-induced hyperuricemia with allopurinol: Male Sprague-Dawley rats (150-200 g) were housed in standard conditions and fed control (n=7) or 60% fructose diet (Harlan, Madison, Wis., n=14) for 10 weeks. "Control diet" contains 46% carbohydrate, which is mainly composed of starch whereas the fructose diet contained 60% fructose as the carbohydrate. The caloric content of these diets are 3.1 kcal/g and 3.6 kcal/g, respectively. At 4 weeks, blood sample were obtained at 11 am in the morning after 4 h fasting. Half of the fructose-fed rats were administered allopurinol (AP, 150 mg/L in the drinking water) (Sigma, St. Louis, Mo.) for an additional 6 weeks to lower serum uric acid. Fresh drinking water containing allopurinol was replaced every 2 days. Rats were divided into 3 groups: Control; Fructose (Fr); and Fr+AP. At 10 weeks an oral glucose tolerance test was performed, in which rats were fasted overnight (16 hours), and then administered 1.5 g/kg OGTT (50% glucose solution) by gavage. Blood was sampled at 0, 30, 60, 120 min for blood glucose and serum insulin measurement. Rats were then sacrificed.

Prevention of fructose-induced hyperuricemia with allopurinol: To assess the effect of preventing hyperuricemia during the period of the study, allopurinol was initiated on the day when fructose diet was given (from week 0 to Week 8). Three groups (control, Fr, and Fr+AP; n=8 each) were designed for this prevention study. Body weight was measured every 2 weeks. Food consumption was measured for 3 days at 8 weeks.

The effect of lowering of uric acid by either allopurinol or Benzbromarone (BZ) on body weight and food consumption: In this experiment, the effect of BZ, a uricosuric agent (150 mg/L in the drinking water) (Sigma, St. Louis, Mo.), was also examined to confirm the effect of lowering of uric acid on body weight and food intake. Fresh drinking water containing Benzbromarone was replaced every 2 days. Three groups (control, AP, and BZ; n=8 each) were studied. All groups were fed with "Control diet" for 8 weeks. Body weight and the consumption of food were measured weekly for 8 weeks.

Comparison between 60% dextrose and 60% fructose on the development of metabolic syndrome and the effect of lowering uric acid with Benzbromarone: Rats were pair-fed with 60% dextrose diet or 60% fructose diet for 4 weeks, which are isocaloric. Since Experiment II showed that each rat normally eats 25-30g/day, the inventors administered 25 g of diet to each rat every day. At 4 weeks, total food intake per animal was calculated from the food left over. Total food intake is the subtraction of the left-over food from total administered food (1425 g/rat/28days). In addition to the above two groups, a third group of fructose fed rats were administered BZ. Body weight was measured weekly. At 4 weeks, after 5 h fasting, insulin, triglyceride and uric acid were measured. All protocols were approved by the Animal Care Committee of the University of Florida.

Measurements: Systolic blood pressure was assessed as the mean value of 3 consecutive measurements obtained in the morning using a tail-cuff sphygmomanometer (Visitech BP2000, Visitech Systems, Inc., Apex, N.C.). All animals were preconditioned for blood pressure measurements 1 wk before each experiment. Serum uric acid was measured by uricase method. Blood glucose was measured with the ONE TOUCH system (Johnson&Johnson, Milpitas, Calif.). Rat insulin was measured by ELISA (Crystal Chem. Inc., Chicago, Ill.). Insulin sensitivity index was calculated using the formula of Matsuda and DeFronzo (10,000/square root of [fasting glucose×fasting insulin]×[mean glucose×mean insulin during OGTT]), which is highly correlated (r=0.73, p<0.0001) with rate of whole-body glucose disposal during the euglycemic insulin clamp (Matsuda M and DeFronzo R A, Insulin sensitivity indices obtained from oral glucose tolerance testing: comparison with the euglycemic insulin clamp, *Diabetes Care* 22: 1462-1470, 1999). Serum lipids were measured with an autoanalyzer (VETAce, Alfa Wassermann Inc, West Caldwell, N.J.) or Triglyceride-SL assay kit (Diagnostic chemicals Limited, Charlottetown, PE, Canada).

Vasorelaxation of rat Aortic Artery (AA) segments: Rat AA segments (1-0.5 mm diameter×3-4 mm length) were isolated from the 2- to 3- month-old rats, AA segments were suspended in individual organ chambers (Radnoti Four-Unit Tissue Bath System) with 5 ml in Earl's solution, oxygenated with 95% O2 and 5% CO2 at 37° C. After 1 hr equilibration of resting force of 1.5 g, vascular smooth muscle cell or endothelium integrity in this AA segment was confirmed by monitoring 0.5 μM U-46619 (a thromboxane A2 mimetic, sigma)-mediated AA contraction or acetylcholine (5 μM)-mediated vasodilation, respectively. After washing several times, the segments were incubated with various concentration of uric acid (0-15 mg/dl) in organ bath chamber for 30 min. Stable construction was induced by 0.5 μM U-46619 for 10 min prior to acetylcholine-induced vasorelaxation. The vascular tensions were continuously monitored with an isometric force transducer (Harvard Apparatus, Holliston, Mass.). To standardize the data, U-46619-induced stable increase in vascular tone was set as 100%.

Statistical analysis. All values presented are expressed as mean±SD and analyzed by one-way analysis of variance (ANOVA) or by unpaired Student's t test. Significance was defined as p<0.05.

Results

In Vivo Study

Serum uric acid levels, systolic blood pressure, and fasting insulin levels were elevated in fructose-fed rats compared to rats fed a control diet at 4 weeks (Table 1). In addition, the body weight of fructose-fed rats tended to increase compared to rats fed a normal diet (Table 1). These data demonstrate that fructose feeding induces early features of the metabolic syndrome in rats.

Figure 9:
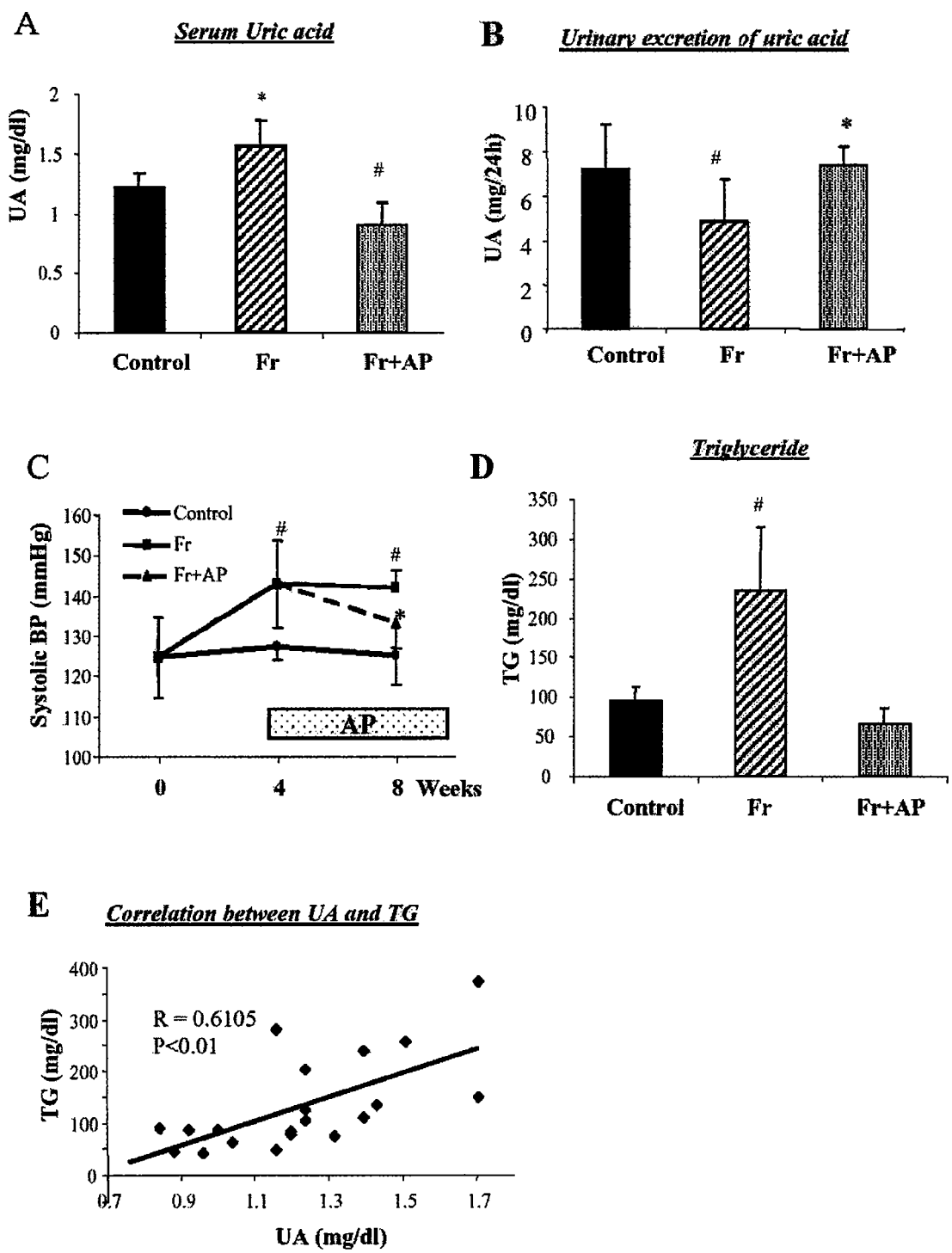
FIG. 9. Effects of allopurinol treatment for hypuricemia on the metabolic parameters in Fructose-fed Rats. Fructose-fe (Fr) are weeks and this is prevented by allopurinol (AP; 150 m $p<0.01$ vs. con $<0.05$ vs. Fr.) (B) Fructose reduced urinary excretion of uric acid at 9 weeks and this is prevented by allopurinol. (*$p<0.01$ vs. Fr; #$p<0.05$ vs. control.) (C) Hypertension develops in fructose-fed rats, which is significantly reduced with allopurinol (#$p<0.01$ vs. control, and Fr) (D) Serum triglycerides are increased in fructose-fed rats, andthis completely prevented by allopurinol (#$p<0.01$ vs. control, and Fr+AP). (E) The serum triglyceride level correlates directly with the serum uric acid. Data are mean±SD.

In order to examine the role of uric acid in this model, half of the fructose-fed rats were treated with allopurinol (a xanthine oxidase inhibitor) for 6 additional weeks. This treatment was effective at lowering uric acid, whereas the fructose-fed rats that did not receive treatment continued to be hyperuricemic (FIG. 9A). In addition, the inventors examined the urinary excretion of uric acid in these animals to clarify the mechanisms of hyperuricemia in fructose-fed rats. As shown in FIG. 9B, fructose-fed rats had lower urinary excretion of uric acid. Interestingly, allopurinol prevented the reduced excretion of uric acid in fructose-fed rats.

Fructose-fed rats treated with allopurinol showed an improvement in the metabolic syndrome. Allopurinol significantly reduced systolic blood pressure in fructose-fed rats (FIG. 9C), although pressures remained higher than that observed in control rats. Fructose-fed rats also developed marked hypertriglyceridemia that was abolished by allopurinol treatment (FIG. 9D). The reduction in serum uric acid correlated directly with the decrease in triglyceride levels (FIG. 9E). Fructose-fed rats also showed an increase in body weight compared to controls. Allopurinol prevented the increase in body weight although this did not reach significance (522±57 g in Fr vs. 470±28 g in control, and 474±37 g in Fr+AP, p=NS).

Figure 10:
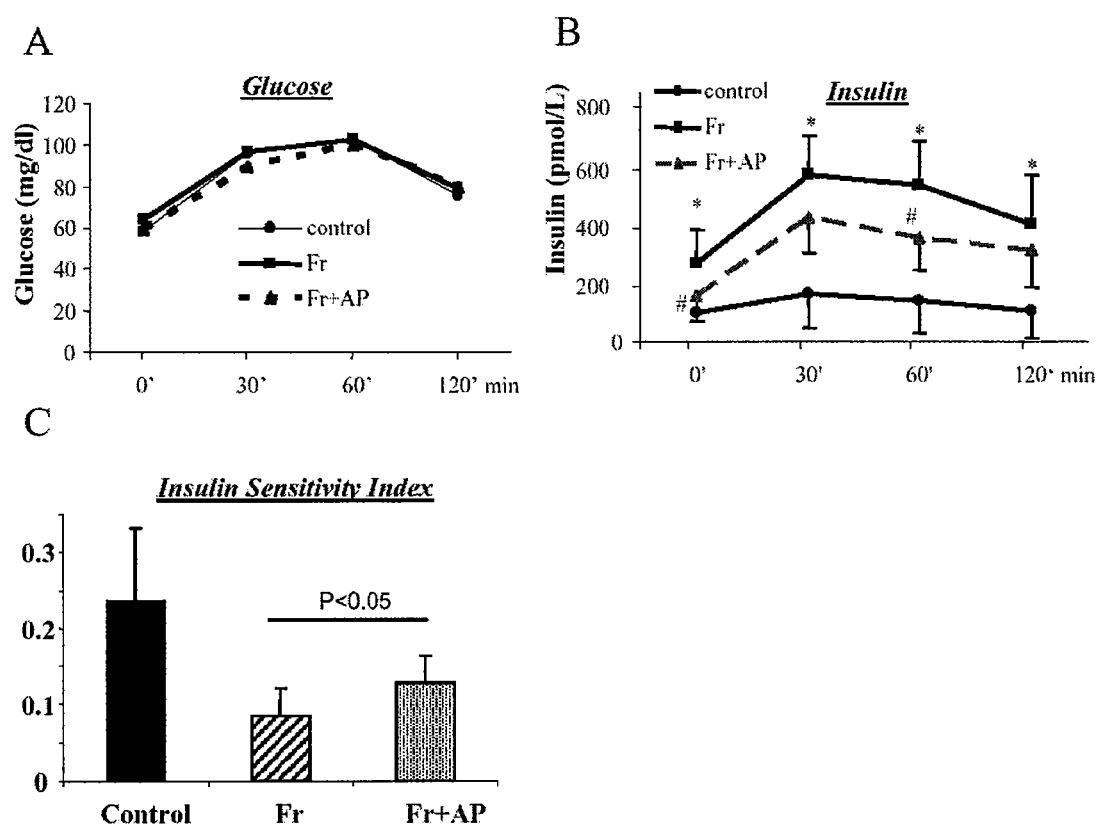
FIG. 10. Effect of allopurinol treatment on glucose metabolism in Fructose-fed rats. (A) Glucose tolerance test at 10 weeks. Similar blood glucose levels were observed in all groups. (B) Plasma insulin levels following the glucose tolerance test. Fructose ingestion was associated with fasting and postprandial hyperinsulinemia. Allopurinol (AP; 150 mg/L) prevented basal hyperinsulinemia and significantly reduced postprandial hyperinsulinemia. (*$p<0.01$ vs. control; #$p<0.05$ vs. Fr.) (C) Insulin sensitivity index (ISI). Insulin sensitivity was reduced with fructose diet and improved by allopurinol. All data are means±SD. Statistical analysis among three groups were analyzed by ANOVA with Bonferoni correction in Figure B. (*$p<0.01$ vs. control; #$p<0.05$ vs. Fr.). Comparison was done between Fr and Fr+AP using unpaired t test in FIG. C.

While no groups developed fasting or postprandial hyperglycemia (FIG. 10A), fructose-fed rats developed fasting hyperinsulinemia that was reversed with allopurinol (FIG. 10B). Postprandial hyperinsulinemia also occurred in fructose-fed rats administered an oral glucose tolerance test, and this was partially but significantly lower in allopurinol-treated rats (FIG. 10), resulting in improved insulin sensitivity (FIG. 10C).

Figure 11:
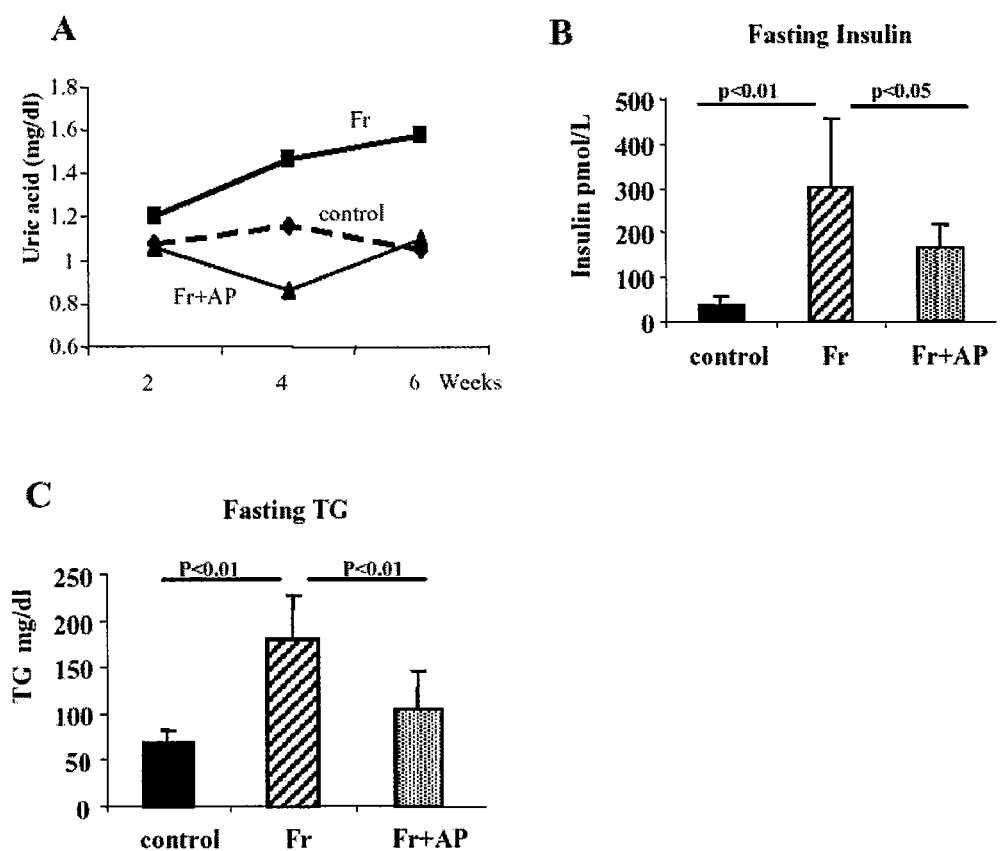
FIG. 11. Blocking of hyperuricemia in fructose-fed rats with allopurinol prevents features of the metabolic syndrome. (A) Allopurinol (AP; 150 mg/L) prevented the rise in uric acid in fructose-fed rats. (#, $p<0.05$ vs con, Fr+AP) (B) Allopurinol treatment was associated with significantly lower fasting insulin levels compared to fructose-fed rats at 8 weeks. (C) Allopurinol also prevented the increase in BW induced with fructose. Statistical analysis among three groups was analyzed by ANOVA with Bonferoni correction.

The inventors also examined the effectiveness of allopurinol in preventing as opposed to treating rats with fructose-induced metabolic syndrome. Allopurinol was given simultaneously with the fructose diet from the starting point to avoid fructose-induced hyperuricemia. As shown in FIG. 11A, the elevation of uric acid by fructose diet was prevented over the 6 week period in fructose-fed rats. Allopurinol treated rats had significantly lower fasting insulin levels compared to fructose-fed rats (FIG. 11B) and the development of hypertriglyceridemia was completely prevented (FIG. 11D). In addition, while fructose-fed rats gained weight compared to control rats (456±24 vs. 414±24 g, final weights in Fr vs. control, p<0.01), allopurinol treated rats had lower weight gain (final weight 426±26 g, p<0.05 vs. Fructose-fed rats). At 8 weeks, total food intake over 3 days in fructose-fed rats was slightly higher (92±2 g) compared to that of the Fructose+ Allopurinol group (88±4 g), although this did not reach statistical significance. The observation that administration of allopurinol to fructose fed rats prevented obesity led to additional studies to ensure that allopurinol did not have specific effects on food intake or body weight. To address this possibility, allopurinol or benzbromarone (a uricosuric) was administered to rats on control diets for 8 weeks. A third group received control diet alone. Total food consumption at 8 weeks and final body weight were not different among the three groups (Table 2).

Finally, the inventors compared the effects of 60% Dextrose diet and 60% Fructose diet on the development of metabolic syndrome. In this experiment food intake was controlled so that each group received the same intake of calories and had the same weight gain. Nevertheless, only the fructose fed rats developed hyperuricemia, hypertriglyceridemia, and hyperinsulinemia (Table 3). Importantly, these effects observed in fructose fed rats were significantly improved by lowering uric acid levels with the uricosuric agent, benzbromarone (Table 3).

In Vitro Studies.

Figure 12:
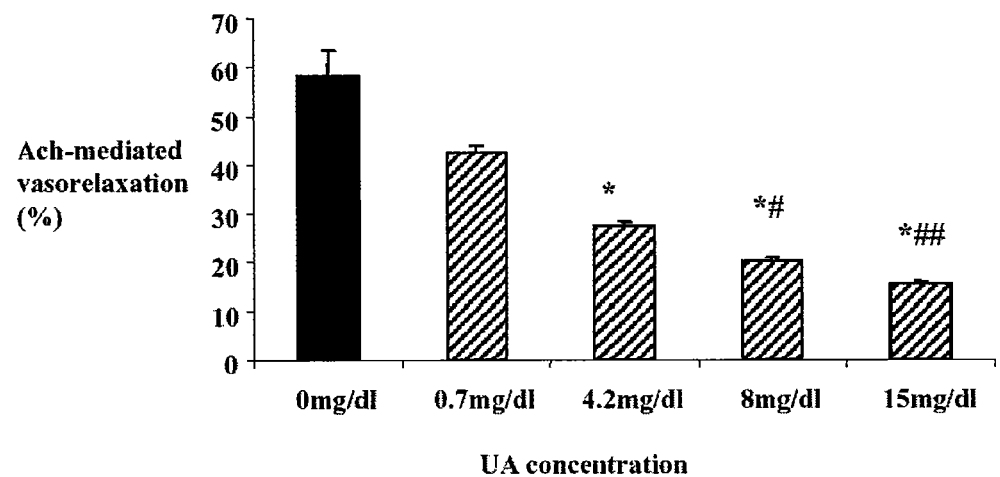
FIG. 12. Uric Acid Inhibits Acetylcholine-Mediate Vasodilation in Rat Aortic Artery Segments. Acetylcholine (5 μM)-induced vasorelaxation was assessed in the presence of various concentration of uric acid for 10 min after stable construction by U-46619 (0.5 μM). n=4, *$p<0.01$ vs. control, #$p<0.05$ vs. 0.7 mg/dl, ##$p<0.01$ vs. 0.7 mg/dl.

Endothelial dysfunction is common in metabolic syndrome. It is known that impaired nitric oxide response to insulin may be a mechanism for the development of insulin resistance (Shinozaki K, Kashiwagi A, Nishio Y, Okamura T, Yoshida Y, Masada Toda N, and Kikkawa R, Abnormal biopterin metabolism is a major cause of impaired endothelium-dependent relaxation through nitric oxide/O2— imbalance in insulin-resistant rat aorta, *Diabetes* 48: 2437-2445, 1999). Previously, uric acid has been shown to potently reduce NO levels in cultured bovine endothelial cells (Khosla U M, Zharikov S, Finch J L, Nakagawa T, Roncal C, Mu W, Krotova, Block E R, Prabhakar S, and Johnson R J, Hyperuricemia induces endothelial dysfunction, *Kidney Int* 67: 1739-1742, 2005). To further examine this relationship, the inventors examined the acute effect of uric acid on acetylcholine-induced vasodilation of rat aortic artery rings. As shown in FIG. 12, uric acid dose-dependently blocked the vasorelaxation of aortic arterial rings in response to acetylcholine.

EXAMPLE 3

Treatment or Delaying the Progression of Diabetic Nephropathy

The inventors hypothesize that an uncoupling of VEGF with endothelial NO might contribute to the vascular complications observed in diabetes. Indeed, the inventors were able to demonstrate that uncoupling of VEGF with endothelial NO could stimulate an excessive endothelial cell proliferation under high glucose conditions. To test their hypothesis in an in vivo model of diabetes, the inventors utilized eNOS KO mice which are incapable of endogenously producing endothelial cell NO. The inventors performed experiments to determine if diabetic mice lacking endothelial NO synthase might be predisposed to diabetic nephropathy.

Methods

Experimental Animals

Experiments were performed following protocol approval by the Animal Care and Use Committee of the University of Florida (IACUC). C57B1/6J mice (C57BL6) and C57BL/6JNos3tm1Unc (eNOS KO mice) (Jackson Laboratory, Bar Harbor, Me.) aged 8 weeks were rendered diabetic with intraperitoneal injections of streptozotocin (STZ) (100 mg/kg/day for 2 consecutive days) freshly dissolved in 0.1M citrate buffer (pH 4.5). Development of diabetes (defined by blood glucose greater than 250 mg/dL) was verified 1 week after the first STZ injection with ONE TOUCH system (Johnson & Johnson, Milpitas, Calif.). For blood sugar control, a single insulin pellet (Linshin Canada Inc, Ontario, Canada) was implanted subcutaneously for 5 months. Blood glucose was monitored every 2 weeks and if the fasting blood glucose was >200 mg/dl, an additional insulin pellet was inserted. Mice were housed in the animal care facility with 12-hour light/dark cycle and allowed free access to food and water. Body weight was recorded monthly. At 3 and 5 months, mice were euthanized for histological analysis. A total of 6 groups were examined with 10 mice for each group at starting points. Non-diabetic (non-DM), diabetic (DM), and diabetic mice (C57BL6 and eNOS KO) with insulin treatment (DMIns) were examined. Systolic blood pressure was assessed as the mean value of 5-10 consecutive measurements obtained in the morning using a tail-cuff sphygmomanometer (Visitech BP2000, Visitech Systems, Inc., Apex, N.C.). BUN was measured by BUN assay (Diagnostic chemicals limited, PE, Canada). Urine in bladder was obtained for urinary albumin excretion at sacrifice. Albumin-to-Creatinine ratio was measured with Albuwell M (Exocell Inc., Philadelphia, Pa.) and Liquid Creatinine Assay (Bioquant, San Diego, Calif.), respectively.

Renal Histology

Kidneys were fixed in Fekete's fixative (mixture of ethanol, distilled water, 37% formalin and glacial acetic acid), and embedded in paraffin. 2-μm sections were stained with the periodic acid-Schiff reagent (PAS) or the periodic acid-methenamine silver (PAM) and counterstained with hematoxylin. Indirect immunoperoxidase staining was performed using antibodies to the endothelial antigen, thrombomodulin (TM) (Yuzawa Y, Brentjens J R, Brett J, Caldwell P R, Esposito C, Fukatsu A, Godman G, Stern D, Andres G: Antibody-mediated redistribution and shedding of endothelial antigens in the rabbit. *J Immunol* 150: 5633-5646, 1993) or CD34 (BD Pharmingen, San Jose, Calif.) (Fina L, Molgaard H V, Robertson D, Bradley N J, Monaghan P, Delia D, Sutherland D R, Baker M A, Greaves M F: Expression of the CD34 gene in vascular endothelial cells. *Blood* 75: 2417-2426, 1990), and to vascular smooth muscle cells with anti-smooth muscle actin (Abcam, Cambridge, Mass.). To detect endothelial cell proliferation, double immunostaining was performed with an antibody to the proliferating cell nuclear antigen, Ki67 (Abcam, Cambridge, Mass.) and thrombomodulin. Color was developed using DAB as a chromogen. In double staining, Bjoran Purple (BioCare Medical, Concord, Calif.) was used for thrombomodulin.

Quantification of Morphology

All quantifications were performed in a blinded fashion. Using coronal sections of the kidney, all glomeruli (100-200 of glomeruli per each animal) were examined. Glomerular mesangial expansion, mesangiolysis, and nodular lesions were evaluated. The percentage of mesangiolysis was calculated as the number of glomeruli with mesangiolysis divided by that of total glomeruli. Arteriolar morphology was assessed by indirect peroxidase immunostaining for alpha-smooth muscle actin. Only vessels which were adjacent to glomeruli in the outer cortex and possessed flattened endothelial cells were selected for arterioles as previously described (Mazzali M, Kanellis J, Han L, Feng L, Xia Y Y, Chen Q, Kang D H, Gordon K L, Watanabe S, Nakagawa T, Lan H Y, Johnson R J: Hyperuricemia induces a primary renal arteriolopathy in rats by a blood pressure-independent mechanism. *Am J Physiol Renal Physiol* 282: F991-997, 2002). Afferent arteriolar wall thickness was measured by computer image analysis. For each arteriole, the outline of the vessel and its internal lumen (excluding the endothelium) were generated by using computer analysis to calculate the total wall area (outline-inline) in a minimum of 12 arterioles. Vessels that were cross-sectioned or not sectioned transversally, providing an asymmetrical wall, were excluded from the present study. Proliferating endothelial cells were identified by double staining with Ki67 and TM or CD34.

Real Time PCR

To quantify mRNA expression for VEGF, real time PCR was performed as described previously (Nakagawa T, Lan H Y, Zhu H J, Kang D H, Schreiner G F, Johnson R J: Differential regulation of VEGF by TGF-beta and hypoxia in rat proximal tubular cells. *Am J Physiol Renal Physiol* 287: F658-664, 2004). Briefly, after 1 μg of total RNA was converted to cDNA with Platinum PCR supermix (Biorad), PCR was performed with mouse VEGF or GAPDH primers mixed with SYBR Green JumpStat Taq ReadyMix (Sigma) using a DNA Engine OPTICON (MJ Research, Waltham, Mass.) as follows: 94° C. for 5 min, then 35 cycles of denaturation at 94° C. for 30 sec, annealing at 61° C. for 1 min and extension at 72° C. for 90 sec. The sizes of amplicons were 111 by (mouse VEGF) (Emanueli C, Salis M B, Van Linthout S, Meloni M, Desortes E, Silvestre J S, Clergue M, Figueroa C D, Gadau S, Condorelli G, Madeddu P: Akt/protein kinase B and endothelial nitric oxide synthase mediate muscular neovascularization induced by tissue kallikrein gene transfer. *Circulation* 110: 1638-1644, 2004). Reaction specificity was confirmed by electrophoretic analysis of products in 2% agarose gel prior to real-time RT-PCR and bands of expected size were detected. Ratios to GAPDH mRNA were calculated for each sample and expressed as mean±SD.

Statistical Analysis

All values presented are expressed as mean±SD. The unpaired Student's t-test was used to determine statistical difference between two experimental groups. Significance was defined as $p<0.05$.

Results

Figure 3:
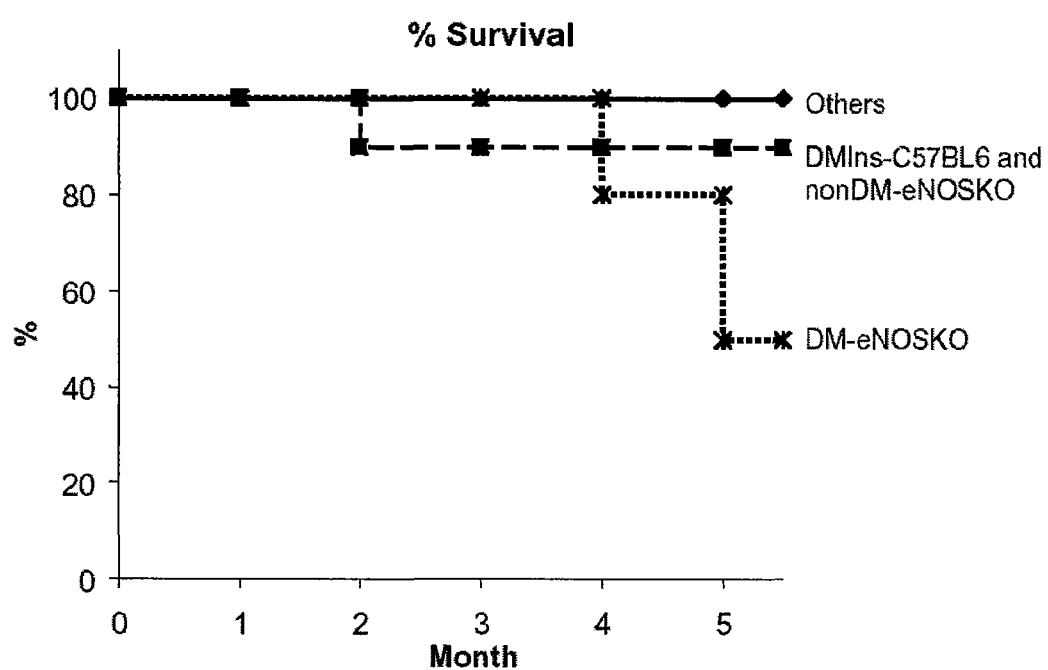
FIG. 3. Survival rate of diabetic eNOS KO mice at 5 months. NonDM; non diabetic mice. DMIns; diabetes with insulin treatment.

General parameters. The induction of type 1 diabetes by streptozotocin resulted in equivalent hyperglycemia in C57BL6 and eNOS KO mice when measured at 3 and 5 months, as shown in Table 4. However, loss of body weight was more severe in diabetic eNOS KO mice compared to diabetic C57BL6 mice. Systolic blood pressure was higher in non-diabetic eNOS KO mice at 3 months but fell to lower levels that wildtype controls at 5 months. Indeed, blood pressure was unmeasurable in 2 out of 6 diabetic eNOS KO mice at 5 months whereas 2 other diabetic eNOS KO mice demonstrated low blood pressures of 92 and 104 mmHg, respectively. Survival of diabetic eNOS knockout mice was also lower at 5 months compared to diabetic wild type mice (FIG. 3).

Insulin treatment was associated with significant improvements in blood glucose levels in both wildtype and eNOS knockout mice. Interestingly, insulin treatment significantly improved blood sugar, blood pressure, and survival in eNOS knockout mice (Table 4 and FIG. 3). Elevated blood pressure at 3 months was improved with insulin treatment in eNOS knockout mice, while lower blood pressures at 5 months was also largely prevented by insulin treatment.

Renal function and gross morphology. Diabetes-induced renal hypertrophy was more pronounced in eNOS KO mice (Table 4). Diabetic wildtype and eNOS knockout mice demonstrate higher urinary albumin excretion as well as high BUN levels at 3 months. However, urinary albumin excretion and BUN levels were higher in eNOS knockout mice compared to diabetic wildtype mice at 5 months (Table 4). The administration of insulin at doses that resulted in normalization of blood sugar prevented the development of renal hypertrophy, proteinuria and renal dysfunction both in the wildtype and eNOS knockout mice (Table 4).

Glomerular Histology

Figure 4:
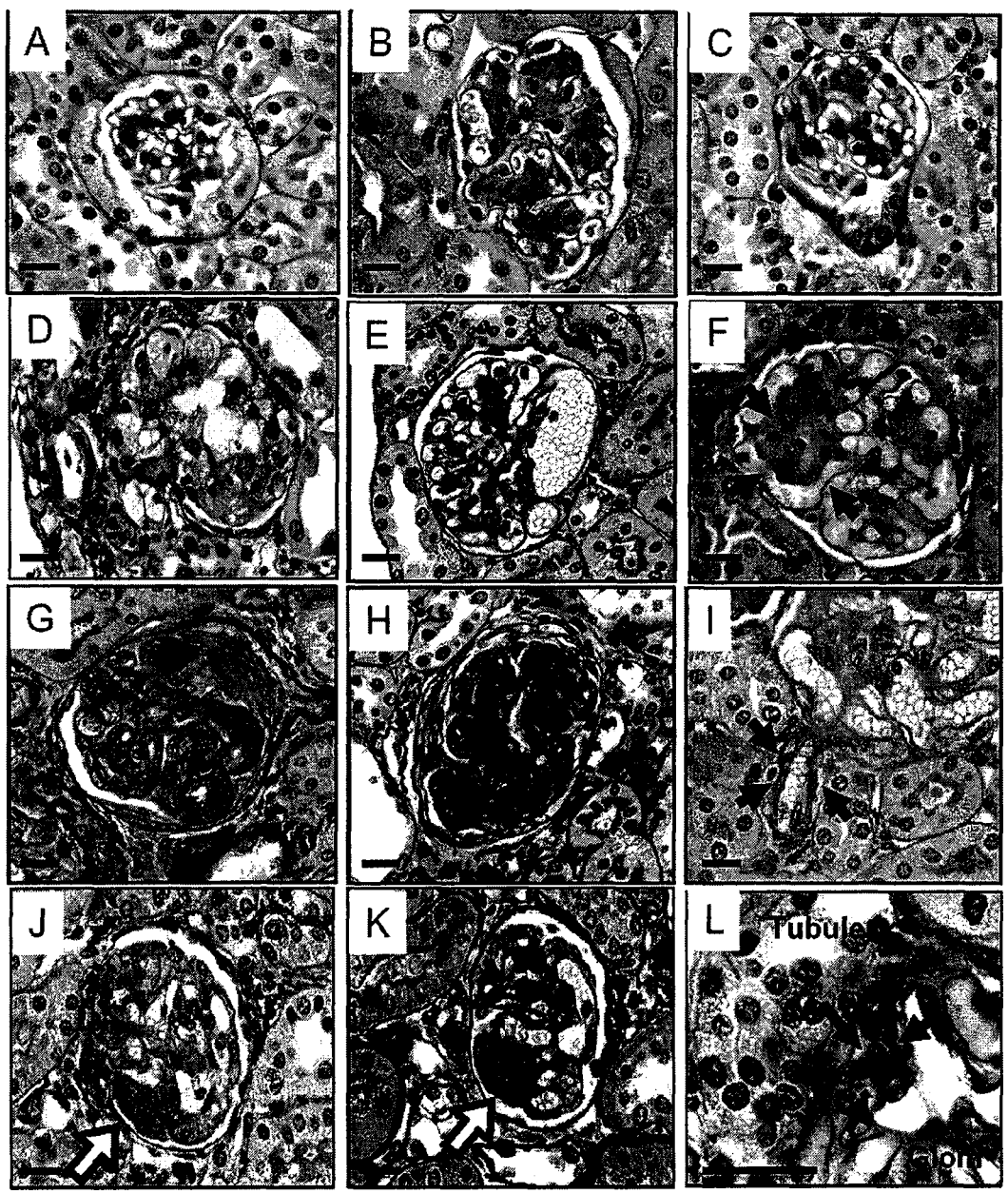
FIG. 4. Histology in glomeruli from C57BL6 and eNOS KO mice. (A-K; ×1000, L; ×2000) (A) glomerulus in non-diabetic C57BL6 mice at 3 months. (B) diabetic C57BL6 mice at 3 months, (C) non-diabetic eNOS KO mice at 3 months. (D) diabetic eNOS KO mice at 3 months. Mesangiolysis can be observed in glomerulus. (E) Glomerular microaneurysm in diabetic eNOS KO mice at 3 months. (F) Nodular glomerular expansion in diabetic eNOS KO mice at 5 months. (G) Nodular lesion with acellular PAS-positive material in diabetic eNOS KO mice at 3 months. (H) Mesangiolysis Diffuse glomerulosclerosis with fibrillar mesagial matrix in diabetic eNOS KO mice at 3 months. (I) Arterioler hyalinosis (arrow) associated with glomerular mesangiolysis in diabetic eNOS KO mice at 5 months. (J) Nodular glomerulosclerosis (arrow) in diabetic eNOS KO mice at 5 months. (K) Nodular glomerulosclerosis on PAM staining in serious section of (J) in diabetic eNOS KO mice at 5 months. (L) (×2000) Hyalinosis (arrow) at vascular pole of glomerulus in diabetic eNOS KO mice at 5 months. Size Bar; 10 μm FIG. 5. Correlation between blood glucose and renal injury at 3 months. (A) Mesangial expansion in C57BL6 and eNOS KO mice. (B) Mesangiolysis in C57BL6 and eNOS KO mice FIG. 6. Arteriolar lesion in diabetic eNOS KO mice at 3 months. (A) Inner lumen size in afferent arteriole. a; $p<0.01$ vs. C57BL6, b; $p<0.05$ vs. non-DM in eNOS KO mice. (B) Inner lumen of afferent arteriole in diabetic eNOS KO mice. Glomerulus with mesangiolysis is associated with dilated arteriole. (C) Wall area of afferent arteriole. (D) Wall area of arteriole in diabetic eNOS KO mice (E) Immunohistochemistry for Smooth muscle actin (SMA) in afferent arteriole in non-DM C57BL6 (×1000). Brown color indicates SMA staining. (F) Immunohistochemistry for Smooth muscle actin (SMA) (Brown color) in afferent arteriole in DM eNOS KO (×1000). (G) PAS staining in non-DM eNOS KO mice (×200). (H) Immunohistochemistry for SMA (Brown color) in non-DM eNOS KO mic (×400).
Figure 5:
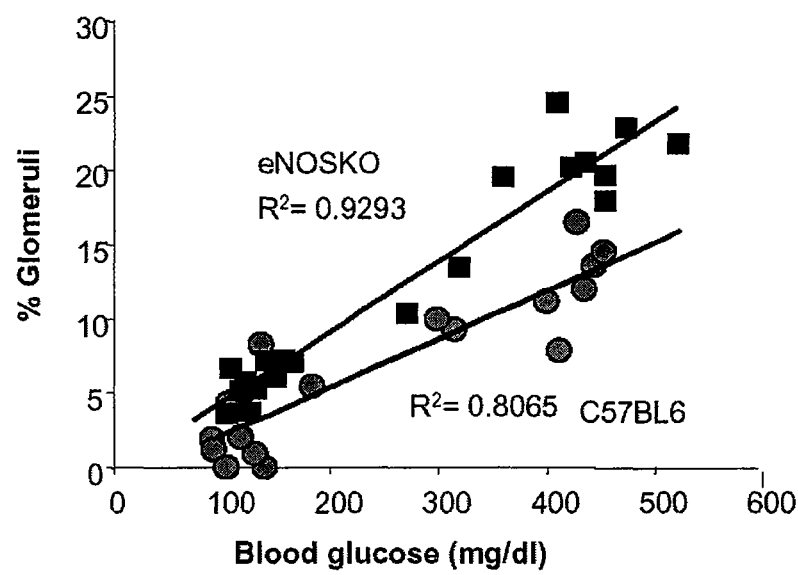
Figure 5:
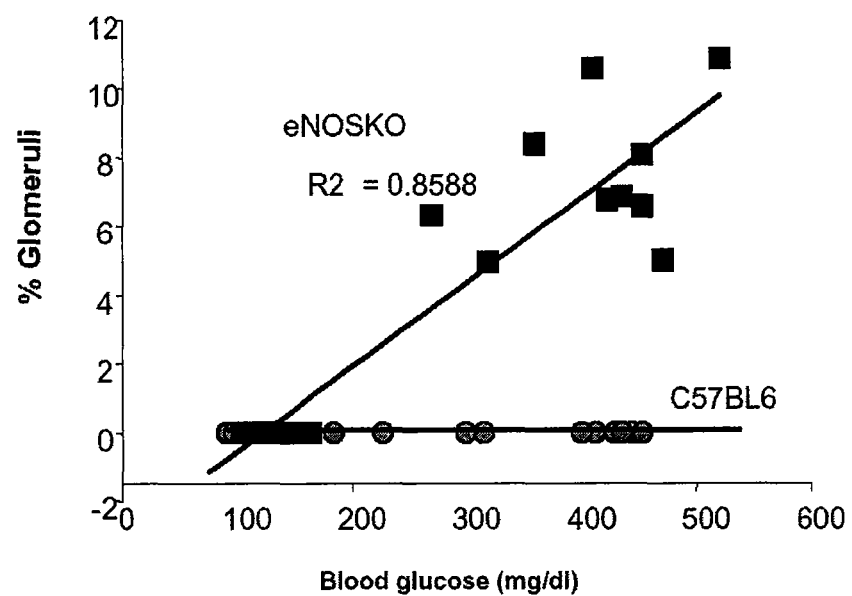

Both C57BL6 and eNOS KO diabetic mice developed mesangial expansion but it was more prominent in the eNOS knockout mice (FIG. 4A, B and Table 5). As shown in FIG. 5, blood glucose levels correlated with mesangial expansion both in C57BL6 mice and eNOS KO mice. Interestingly, glomeruli in eNOS KO were more susceptible to blood glucose than wild type mice in terms of development of mesangial expansion (FIG. 5A). Most importantly, at 3 months there were striking findings in diabetic eNOS KO mice, in which mesangiolysis (FIG. 4D) and glomerular microaneurysms (FIG. 4E) developed. Furthermore, Kimmelstiel-Wilson-like nodular lesions were observed in occasional glomeruli at both 3 and 5 months. These nodular lesions were composed of nodular mesangial expansion (FIG. 4F), acellular PAS-positive material (FIG. 4G), and dense fibrillar mesangial matrix (FIG. 4H). Nodular glomerulosclerosis was demonstrated by serial section of glomeruli with PAS and PAM staining (FIG. 4J and K). Hyalinosis of arterioles (FIG. 4I) or of the vascular pole of the glomerulus (FIG. 4L) were also observed in diabetic eNOS KO mice. Interestingly the presence of significant arteriolar disease in individual glomeruli were often associated with glomerular mesangiolysis (FIG. 4I). Mesangiolysis also correlated with blood glucose levels in diabetic eNOS KO mice (FIG. 5B). In addition, non-diabetic eNOS KO mice rarely developed mesangiolysis at 5 months (Table 6). Interestingly, insulin treatment blocked the development of mesangial expansion, mesangiolysis, and the development of the nodular lesions at 3 and 5 months (Table 5, 6).

Renal Arteriolar Histology

Figure 6:
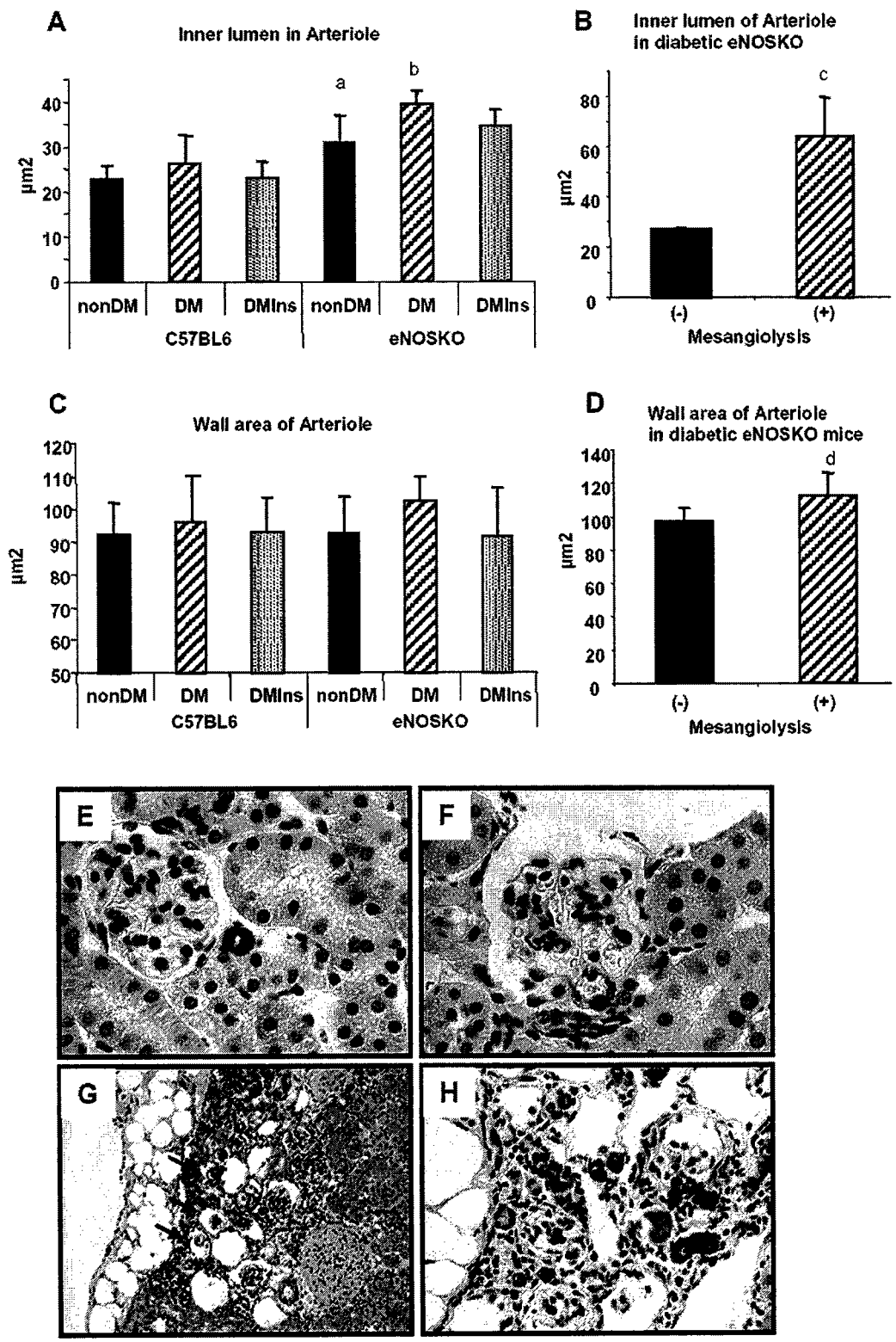

The inventors have previously demonstrated in other models that the development of preglomerular arteriolar disease results in altered autoregulation and can predispose kidneys to progression (Johnson R J, Feig D I, Herrera-Acosta J, Kang D H: Resurrection of uric acid as a causal risk factor in essential hypertension. *Hypertension* 45: 18-20, 2005). The inventors have also shown that preglomerular arteriolar disease occurs with blockade of NO synthesis with L-NAME (Quiroz Y, Pons H, Gordon K L, Rincon J, Chavez M, Parra G, Herrera-Acosta J, Gomez-Garre D, Largo R, Egido J, Johnson R J, Rodriguez-Iturbe B: Mycophenolate mofetil prevents salt-sensitive hypertension resulting from nitric oxide synthesis inhibition. *Am J Physiol Renal Physiol* 281: F38-47, 2001). The inventors therefore examined the morphology of the afferent arteriole in both diabetic and nondiabetic mice. As shown in FIG. 5, the lumen of arterioles of eNOS KO mice were larger than that observed in C57BL6 mice. In animals with diabetes there was a further increase in the inner lumen size in eNOS KO mice compared to non-diabetic C57BL6 mice (FIG. 6A, 6E, 6F). This increase was blocked by insulin treatment (FIG. 6A). On the other hand, the total vascular smooth muscle wall area was not different in these mice (FIG. 6C). Interestingly, glomeruli with mesangiolysis were significantly associated with dilated arterioles (FIG. 6B) as well as an increase in vascular smooth muscle wall area (FIG. 6D) compared to those glomeruli without mesangiolysis.

eNOS KO mice also demonstrated rare focal areas of tubular atrophy with condensed, hypoplastic glomeruli (FIG. 6G). In these areas, the arterioles were severely constricted or occluded (FIG. 6H).

Angiogenesis (Endothelial Cell Proliferation)

Figure 8:
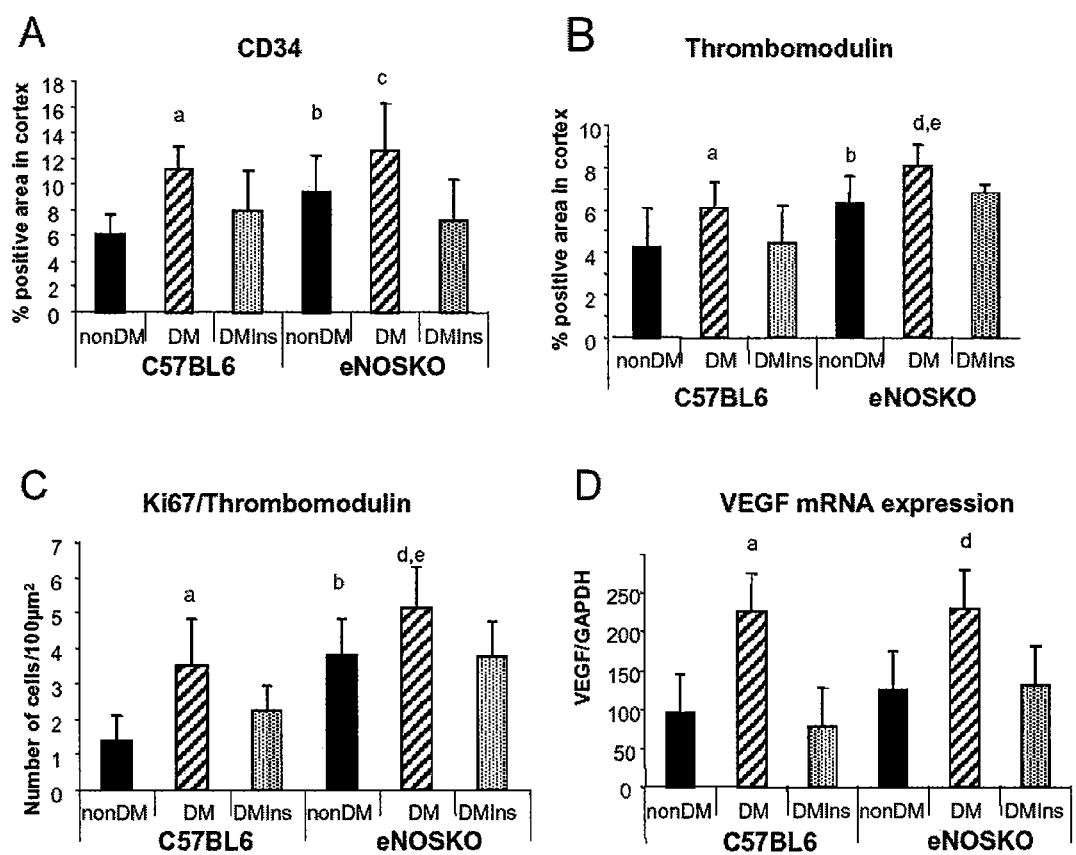
FIG. 8. (A) Quantification of CD34 in cortex. (B) Quantification of Thrombomoduline staining. (C) Cell number with double staining for TM and Ki67 in renal cortex per 100 μm². (H) Real time PCR for VEGF mRNA expression in whole kidney at 3 month. a; $p<0.05$ vs. non-DM and DM Ins in C57BL6. b; $p<0.05$ vs. non-DM in C57BL6. c; $p<0.05$ vs. DMIns in eNOSKO. d; $p<0.05$ vs. nonDM and DMIns in eNOS KO. e; $p<0.05$ vs. DM in C57BL6 nonDM; non-diabetes, DM; diabetes, DMIns; diabetes+Insulin treatment.

VEGF mRNA expression was increased in diabetic C57BL6 and eNOS KO mice (FIG. 8D). Importantly, insulin treatment blocked this up-regulation of VEGF, demonstrating a key role for glucose in regulating VEGF regardless of the status of the endothelial NO system.

Figure 7:
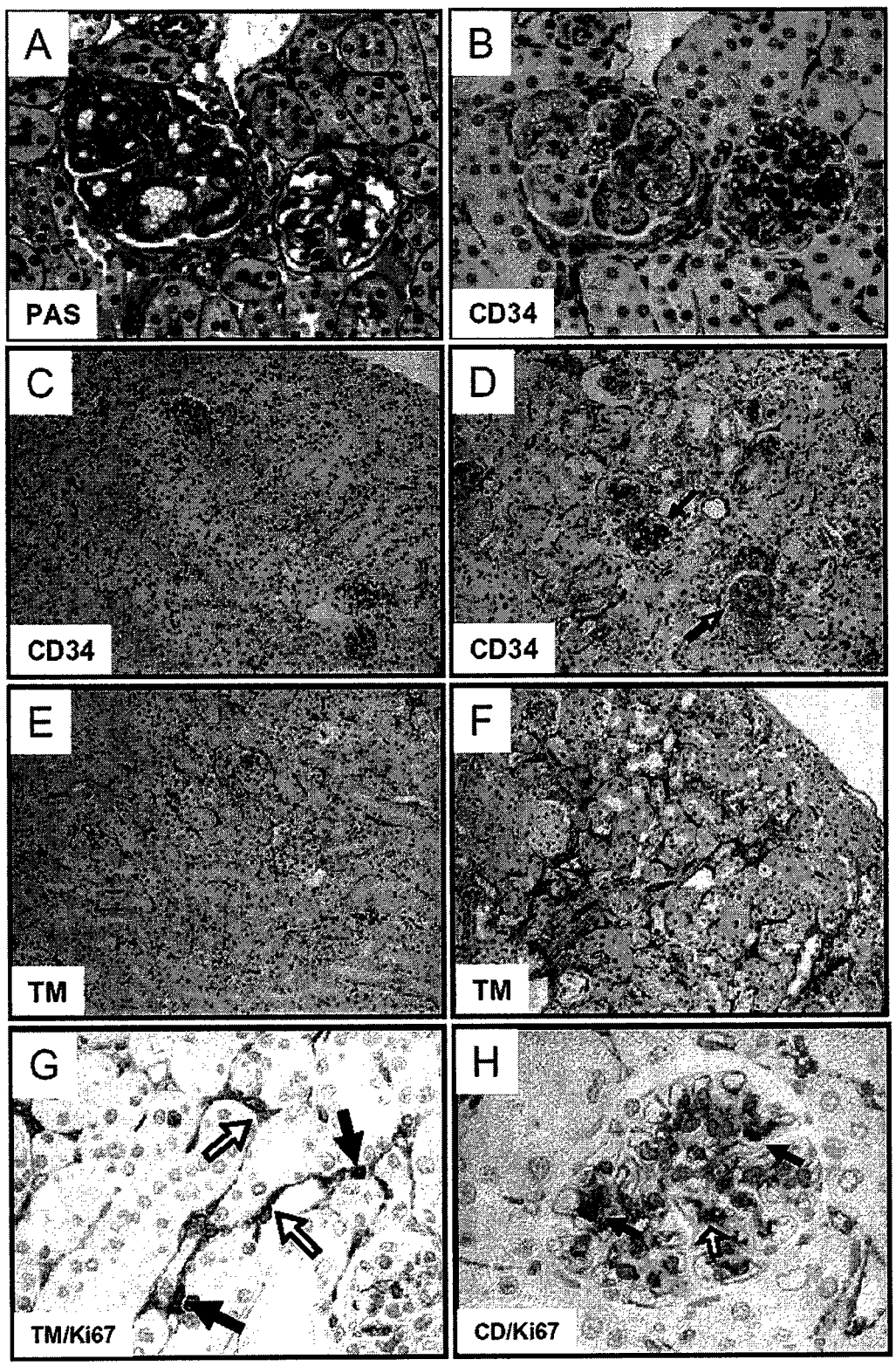
FIG. 7. Endothelial cell proliferation in diabetic eNOS KO mice. (A) PAS staining of injured glomerulus in diabetic eNOS KO mice at 3 months (×630). (B) Immunostaining for CD34. Brown color indicates CD34 staining as a marker of endothelial cell. Blue color indicates counter staining for nucleus with hematoxyline. Loss of endothelial cell is observed in injured glomerulus in diabetic eNOS KO mice at 3 months. (C) Immunohistochemistry for CD34 in non-DM C57BL6 (×200). (D) CD34 in Diabetic eNOS KO kidney (×200). Some glomeruli show strong immunoreactivity (block arrow) whereas some show less endothelial staining (white arrow). (C) Immunostaining for Thrombomodulin (TM) (Brown color) in non-DM C57BL6 (×200). TM is primarily expressed in peritubular capillary. (D) TM in diabetic eNOS KO (×200). (E) Double staining for TM (Bjoran Purple) (white arrow) and Ki67 (Dark brown). Double staining can indicate proliferating endothelial cell (black arrow). (F) Proliferating endothelial cell detected (black arrow) by double staining of glomerular capillary for TM (white arrow) and Ki67 (Dark brown).

Endothelial morphology was assessed by immunostaining for CD34 (Fina L, Molgaard H V, Robertson D, Bradley N J, Monaghan P, Delia D, Sutherland D R, Baker M A, Greaves MF: Expression of the CD34 gene in vascular endothelial cells. *Blood* 75: 2417-2426, 1990) and thrombomodulin (Yuzawa Y, Brentjens J R, Brett J, Caldwell P R, Esposito C, Fukatsu A, Godman G, Stern D, Andres G: Antibody-mediated redistribution and shedding of endothelial antigens in the rabbit. *J Immunol* 150: 5633-5646, 1993). Both diabetic eNOS knockout and wildtype mice showed a generalized increase in endothelial cells in the cortex as noted by immunostaining for either CD34 or thrombomodulin (FIGS. 7 and 8), and this was associated with enhanced endothelial cell proliferation, as noted by double staining with Ki67 and thrombomodulin or CD34 (FIG. 7G, 7H). Both endothelial proliferation and endothelial immunostaining were increased in eNOS diabetic knockout compared to diabetic wildtype mice. Insulin treatment also largely corrected the increase in endothelial cell proliferation and number.

In contrast, focal loss of endothelial cell staining was occasionally observed, particularly in glomeruli displaying mesangiolysis (FIGS. 7A and 7B).

Discussion

In this study, the inventors present a mouse model of diabetic kidney disease that closely resembles human diabetic nephropathy. Diabetic mice lacking the eNOS gene demonstrated classic features of diabetic nephropathy with intrarenal vascular disease, mesangial expansion with mesangiolysis and occasional microaneurysm formation, and with the development of mesangial nodular (Kimmelsteil-Wilson) lesions. These changes could be largely prevented by insulin. Collectively, the data strongly suggests that a relative deficiency in endothelial NO levels may be one of the long-sought risk factors that is critical for the increased susceptibility for nephropathy in subjects with diabetes.

Without being bound to any particular theory, the inventors believe that one potential mechanism by which eNOS knockout mice may be more susceptible to diabetic nephropathy is due to the dysregulation of the VEGF-NO axis. Normally VEGF acts on endothelial cells largely via stimulation of eNOS. However, in the setting where endothelial NO levels are low, an increase in VEGF expression is associated with a marked NO-independent endothelial proliferative response. The inventors have found that elevated glucose can cause this uncoupling in vitro.

Consistent with the uncoupling hypothesis was our observation that endothelial cell staining and proliferation were increased in diabetic eNOS knockout mice compared to diabetic control mice. Importantly, the increased expression of VEGF was blocked in both groups of mice with insulin treatment. This demonstrates that the regulation of VEGF expression appears to be primarily dependent on glucose levels as opposed to endothelial NO levels in this model. In addition, the observation that endothelial staining was greater in eNOS knockout mice compared to wild type mice regardless of presence of diabetes suggests the importance of the uncoupling hypothesis in augmenting the endothelial proliferative response (Nakagawa T, Sato W, Sautin Y Y, Glushakova O, Croker B, Atkinson M A, Tisher C C, Johnson R J: Uncoupling of vascular endothelial growth factor with nitric oxide as a mechanism for diabetic vasculopathy. *J Am Soc Nephrol* 17: 736-745, 2006). In contrast, Murohara et al have reported that eNOS KO mice exhibited impaired angiogenesis in the hindlimb ischemic model (Murohara T, Asahara T, Silver M, Bauters C, Masuda H, Kalka C, Kearney M, Chen D, Symes J F, Fishman M C, Huang P L, Isner J M: Nitric oxide synthase modulates angiogenesis in response to tissue ischemia. *J Clin Invest* 101: 2567-2578, 1998). In their model, however, the ischemic insult failed to increase VEGF expression whereas in our model the primary stimulus appeared to be hyperglycemia.

An interesting finding was that the presence of mesangiolysis was associated with loss of glomerular endothelial cells whereas most other glomeruli showed an endothelial proliferative response in diabetic eNOS KO mice. This heterogeneity of endothelial response could be associated with the heterogeneity of mesangial cell proliferation. Indeed, it has been demonstrated that a glomerulus simultaneously exhibits mesangial proliferation and mesangiolysis in human diabetic nephropathy (Stout L C, Kumar S, Whorton E B: Focal mesangiolysis and the pathogenesis of the Kimmelstiel-Wilson nodule. *Hum Pathol* 24: 77-89, 1993). Furthermore it is also compatible with the evidence that anti-Thy1-induced mesangiolysis in rat is associated with loss of both mesangial and endothelial cells followed by both mesangial and glomerular endothelial cell proliferation (Iruela-Arispe L, Gordon K, Hugo C, Duijvestijn A M, Claffey K P, Reilly M, Couser W G, Alpers C E, Johnson R J: Participation of glomerular endothelial cells in the capillary repair of glomerulonephritis. *Am J Pathol* 147: 1715-1727, 1995).

It is also possible that the deletion of eNOS gene could have altered local endothelial viability and thereby predisposed glomeruli to mesangiolysis (Table 6). However, the fact that the mesangiolysis was largely prevented by insulin treatment suggests that elevated glucose (and/or AGEs) are also likely important factors. However, a high glucose cannot be the sole factor since diabetic C57BL6 mice did not develop mesangiolysis. However, a high glucose could additionally impair endothelial function, and thereby accelerate the development of glomerular injury.

The inventors believe that this new murine model of diabetic nephropathy may be relevant to human diabetic disease. In addition to the similar histological findings, human diabetic nephropathy is also strongly associated with endothelial dysfunction due to the effects of glucose and AGEs, but also because of the frequent elevations in uric acid (Bo S, Cavallo-Perin P, Gentile L, Repetti E, Pagano G: Hypouricemia and hyperuricemia in type 2 diabetes: two different phenotypes. *Eur J Clin Invest* 31: 318-321, 2001.), CRP (Tan K C, Chow W S, Tam S C, Ai V H, Lam CH, Lam K S: Atorvastatin lowers C-reactive protein and improves endothelium-dependent vasodilation in type 2 diabetes mellitus. *J Clin Endocrinol Metab* 87: 563-568, 2002), oxidative stress (Beckman J A, Goldfine A B, Gordon M B, Garrett L A, Keaney J F, Jr., Creager M A: Oral antioxidant therapy improves endothelial function in Type 1 but not Type 2 diabetes mellitus. *Am J Physiol Heart Circ Physiol* 285: H2392-2398, 2003) and asymmetric dimethylarginine (ADMA) (Fard A, Tuck C H, Donis J A, Sciacca R, Di Tullio M R, Wu H D, Bryant T A, Chen N T, Torres-Tamayo M, Ramasamy R, Berglund L, Ginsberg H N, Homma S, Cannon P J: Acute elevations of plasma asymmetric dimethylarginine and impaired endothelial function in response to a high-fat meal in patients with type 2 diabetes. *Arterioscler Thromb Vasc Biol* 20: 2039-2044, 2000; Tarnow L, Hovind P, Teerlink T, Stehouwer C D, Parving H H: Elevated plasma asymmetric dimethylarginine as a marker of cardiovascular morbidity in early diabetic nephropathy in type 1 diabetes. *Diabetes Care* 27: 765-769, 2004) all which are known to reduce endothelial NO bioavailability (Landmesser U, Harrison D G, Drexler H: Oxidant stress-a major cause of reduced endothelial nitric oxide availability in cardiovascular disease. *Eur J Clin Pharmacol*: 1-7, 2005). Since uric acid, CRP, and ADMA tend to be higher in humans than rodents, this could provide a potential explanation why rodents are much less likely to develop classic diabetic renal disease. It is well known that only 30-40% of subjects with type I diabetes will develop significant nephropathy. Based on the findings in this study, the inventors propose that it is the level of endothelial NO that may be one of the critical determinants for whether diabetic subjects are at risk for developing nephropathy. By extension, normalizing uric acid levels in diabetic patients may delay the onset or prevent diabetic nephropathy.

EXAMPLE 4

Treatment of Prevention of Fatty Liver Syndrome

Non-alcoholic fatty liver disease (NAFLD), a more recently appreciated component of the Metabolic Syndrome with a more than 30-fold relative risk in obese individuals, is believed to be the most prevalent form of liver disease worldwide. Fatty liver syndrome is dramatically increased in patients with metabolic syndrome. Liver steatosis associated with obesity results from increased plasma free fatty acids uptake, enhanced rate of de novo fatty acid synthesis, and/or dysregulation of intracellular lipid partitioning in which fatty acid oxidation is impaired and its esterification enhanced (Fromenty B, et al. Diabetes Metab. 2004, 30:121; Festi D, et al. Obes. Rev. 2004, 5:27). As discussed above, the inventors show that fructose enriched diet induces the metabolic syndrome (hyperinsulinemia, hypertriglyceridemia, hyperuricemia and weight gain) in rats at 8 weeks. Further, the inventors realize that fructose is known to cause fatty liver. The inventors demonstrate that administration the uric acid lowering agent, allopurinol, reduces the exhibition of these characteristics. Metabolic syndrome produces an increase triglyceride plasma levels, which likely reflect intracellular triglyceride stores that are responsible for the fatty liver. By logical extension, the inventors assert that reducing the onset of the metabolic syndrome will reduce the onset of fatty liver.

The disclosures of the cited patent documents, publications and references are incorporated herein in their entirety to the extent not inconsistent with the teachings herein. It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method of improving nitric oxide bioavailability in renal arteriole and glomerular cells to treat uric acid-induced diabetic nephropathy in a patient in need, wherein said patient in need has diabetes, a uric acid level higher than 5.5 mg/dl, impaired endothelial function, and elevated albumin excretion, said method comprising administering to said patient a composition comprising a uric acid lowering agent (UALA) according to a regimen effective to maintain said patient's average serum uric acid level at or below 5.5 mg/dl and to increase nitric oxide bioavailability in renal arteriole and glomerular cells, wherein said UALA is a xanthine oxidase inhibitor.

2. The method of claim 1, wherein said xanthine oxidase inhibitor is allopurinol or febuxostat, or both.

3. The method of claim 1, wherein said regimen is effective to maintain said patient's average serum uric acid level at or below 5.5 mg/dl for at least 12 weeks.

* * * * *